United States Patent [19]

Daiberl

[11] 4,286,947
[45] Sep. 1, 1981

[54] INTRA-ORAL ALIGNING ASSEMBLY

[76] Inventor: Karl Daiberl, Untersbergstrasse 4/II r., 8000 München 90, Fed. Rep. of Germany

[21] Appl. No.: 46,498

[22] Filed: Jun. 7, 1979

[30] Foreign Application Priority Data

Jun. 9, 1978 [DE] Fed. Rep. of Germany ....... 2825470

[51] Int. Cl.³ .............................................. A61C 19/04
[52] U.S. Cl. ..................................................... 433/72
[58] Field of Search ......................... 433/72, 71, 68, 75

[56] References Cited
U.S. PATENT DOCUMENTS 3,314,152  4/1967  Frush ................................ 433/72

*Primary Examiner*—Robert Peshock
*Attorney, Agent, or Firm*—Michael J. Striker

[57] ABSTRACT

An aligning assembly for prosthodontic applications has an upper jaw plate, a lower jaw plate, and a pin on one of these plates. The pin has a free end shaped as a spherical segment whose surface is curved rearwardly from the tip through at least 100° of arc towards the shaft of the pin. The other jaw plate has an opening and, due to the shape of the spherical-segment surface, the surface will always be in full circumferential contact with the edge of the opening when the plates are brought together, even though skewing of the plates relative to one another should occur.

33 Claims, 8 Drawing Figures

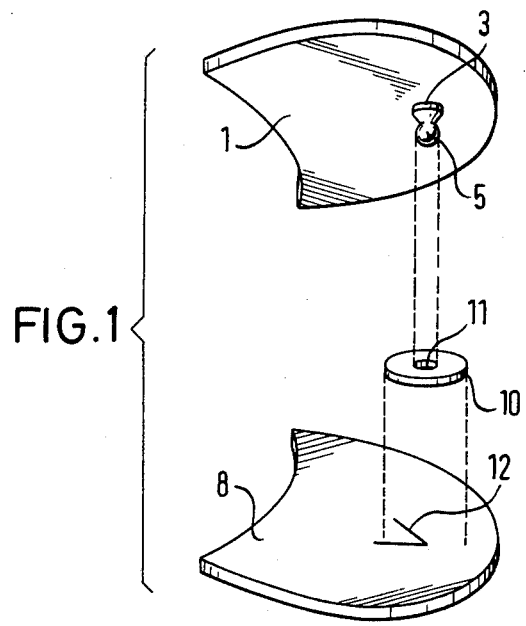
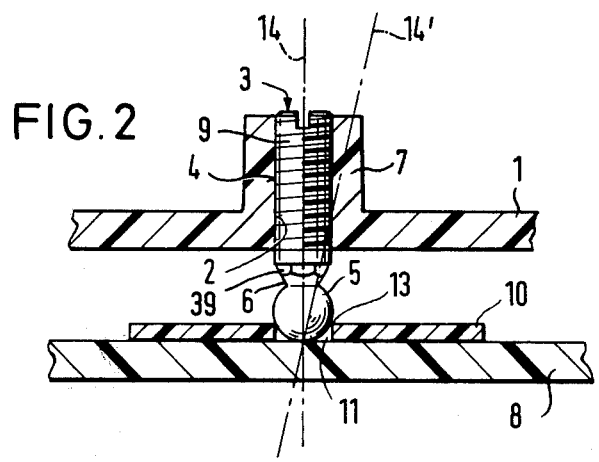

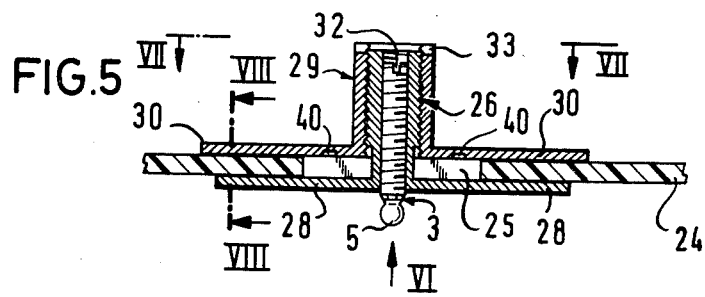
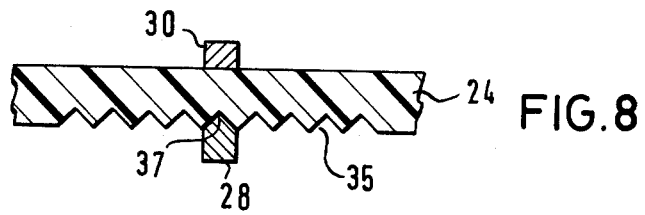
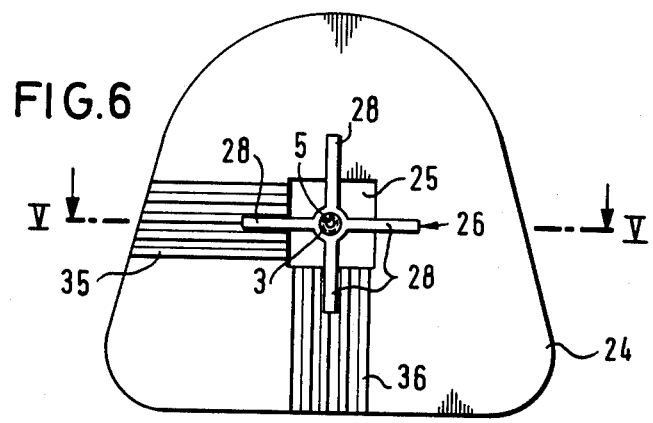
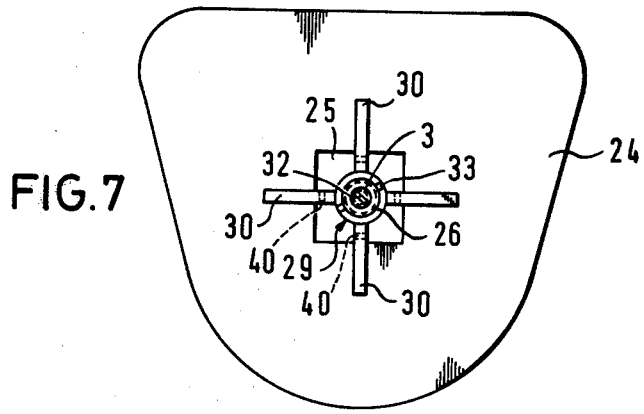

INTRA-ORAL ALIGNING ASSEMBLY

BACKGROUND OF THE INVENTION

This invention relates generally to a dental device, and more particularly to an intra-oral dental device.

Still more specifically, the invention relates to an intra-oral aligning assembly for tooth prostheses, occlusion diagnostic and/or occlusion therapy in general, and more particularly to such an assembly which includes rigid upper jaw and lower jaw components of which one is provided with a through-going tapped bore into which a supporting pin is threaded, the tip of which is insertable into an opening in the area of that surface of the other jaw plate which faces the jaw plate having the tapped bore.

Aligning assemblies of this type are known, for example from U.S. Pat. Nos. 3,068,570 and 3,564,717. When assemblies of this type are used, the two plates are inserted into and fixed in the upper and lower jaw, respectively. Thereafter, the patient is requested to cause his lower jaw to perform sliding movements in anterior-posterior as well as lateral direction, and during these movements the tip of the supporting pin traces on preferably colored surface of the other jaw plate a figure having essentially an arrow-shaped configuration and which is called a Gothic Arch. Thereafter, the dentist places a thin apertured plate onto the other jaw plate in such a manner that the middle of the opening of the apertured plate coincides with the tip of the arrow. In this position the apertured plate is fixed with respect to the other of the jaw plate and thereafter the other jaw plate is again inserted into the mouth of the patient who is then instructed to close his jaws with slight pressure, the purpose being to have the tip of the supporting pin enter into the opening of the apertured plate. The dentist then places dental molding material or the like between the two bite plates in order to fix them in this position relative to one another. After the material hardens the bite plates can be taken out of the patient's mouth as a unit, i.e. in a state in which they are fixed relative to one another.

In the devices known from the prior art the tip of the supporting pin is formed by a sphere which is turnably journalled in an appropriate journal of the tip of the pin shaft. In this manner the pin is constructed somewhat analogously to a ball-point pen, so as to assure that during tracing of the Gothic Arch rolling of the sphere produces ready movement of the tip of the pin with respect to the other bite plate. Of course, the sphere or ball must be so mounted that during the use of the assembly it does not fall out of its support, which means that it must enter the socket holding it to a depth which is greater than its radius.

The opening and closing movement of the lower jaw takes place over a range of approximately the first two centimeters (adjacent the closed position) in a circular path about a center formed by the condyles. The position of the condyles is defined by the concept of the retrograde contact position, which is the starting point of each functional analysis and prosthetic treatment. Therefore, it must not be allowed to change in the determination of the bite height, because it determines the vertical position of the lower jaw with reference to the upper jaw.

Since the opening and closing movement of the lower jaw with the condyle position in retrograde contact position takes place in a circular path, this circular path must be taken into account during the point-like fixation of the selected bite height. Any lack of accuracy in the vertical direction results in an improper bite height, whereas any lack of accuracy in the horizontal direction produces a false condyle position.

With respect to the known assemblies of the type here in question, the accuracy is limited. During the terminal bite position the tip of the supporting pin will meet the arrowhead traced on the other bite plate in cooperation with the opening of the apertured plate in an exact manner only, if the bite plates and the axial directions of the supporting pin tip and the apertured plate opening approach one another in exact parallelism at the end of the jaw movement. Such an exactly parallel approach of the bite plates, the supporting pin tip and the opening in the apertured plate in the terminal phase of the circular movement of the lower jaw cannot be assured in actual practice. It is obtained only in certain fortunate exceptional conditions. In the vast majority of cases the tip of the supporting pin will engage the edge or the inner wall of the opening in the apertured plate prematurely, due to tilting of the pin with reference to the axis of the opening. This results in a wedging effect and a maladjustment of the supporting pin tip and the arrowhead tip. The result is improper registration during the fixation both in the vertical direction (bite height) and in the horizontal direction (condyle position). This results in a condyle shift which is undesirable.

One of the objects of the invention is to eliminate these problems and to produce a device of the type in question which is simple to use and which excludes registration errors to the maximum extent possible, which result from the fact that in the terminal phase of the bite movement deviations with respect to parallelism of the bite plates occur and the circular movement of the lower jaw during the closing movement has a forwardly directed component.

Another disadvantage of the known devices is that the bite plates can be only insufficiently fixed in the upper and lower jaws, because the bite plates are constructed either as narrow strips, or triangular or of hourglass shape. This means that they have few supporting areas which are closely adjacent to one another, so that there is a substantial danger that the bite plates may tilt during the tracing of the Gothic arch and during the final bite.

The determination of the joint-related position of the lower jaw with reference to the upper jaw, during which heads of the jaw joint are centered at the highest points of the cavities of the jaw points, is effected according to the static principle of the three-point support and requires that the supporting pin is centrally arranged. If the supporting pin deviates from the central arrangement in the saggital or transversal direction, a tilting of the lower jaw results which causes a shifting of the heads of the jaw joint in their sockets. This clinical experience is used in the treatment of patients who have the symptoms of myoarthropaty and for whom the heads of the jaw joint are to be therapeutically displaced in the sockets until a reduction of pain or freedom of pain during the final bite has been achieved. In the known devices the supporting pin is adjustable with reference to the bite plate carrying it, only in the direction of the supporting pin axis, which is normal to the bite plate plane. If a change in the supporting pin position is desired in the saggital or transversal directions, the bite plate must be removed from the supporting substrate and subsequently be connected again thereto. This is time consuming and inaccurate, because there is no appropriate reference system.

In German published application No. 2,645,852 it has been proposed to provide an aligning assembly with a three-dimensionally displaceable supporting pin. A threaded sleeve receiving the supporting pin is movable in longitudinal direction of an elongated slot of an intermediate plate and can be fixed with reference to the intermediate plate by means of a set screw. The intermediate plate itself is adjustable in a direction normal to the elongation of the elongated slot, by means of a guide which is inserted in the respective bite plate. To fix the intermediate plate two clamping screws and bars are provided at opposite sides of the intermediate plate which serve to press the bars against the intermediate plate and are threaded into the bite plate. This solution, however, is rather expensive and, in addition, requires a very significant amount of space.

When taking a bite using intra-oral aligning assemblies, it is desired that the retrograde contact position of the condyles in the sockets are fixed under the same pressure loads on the gums and the teeth, as they occur if a definitive tooth replacement is provided. Loading of the gums and of the teeth during the taking of the bite is to correspond to the later loading by the prostheses. This requires readily workable types of bite plates which can reach any desired point of the dental arc and be there positioned. The known devices are too small and too narrow for this purpose and as a consequence disadvantageous tilting moments can arise during the registration and fixation.

For this reason another object of the invention is to provide an intra-oral assembly device of the type in question the bite plate of which can be mounted particularly safely in the upper and lower jaws. Furthermore, the device is to have a three-dimensional adjustability of the supporting pin in a simple manner. The device is to permit a prostheses-simultaneous mounting and to require little room.

SUMMARY OF THE INVENTION

Pursuant to the above objects, and to others which will become apparent hereafter, one aspect of the invention resides in a device of the type in question having a supporting pin the tip of which is a segment of a sphere which is rigidly coupled with the shaft of the pin, and the free part-spherical surface of which reaches from the front end of the pin located on the longitudinal axis of the shaft in all directions rearwardly over an angle of at least 100°, in such a manner that even during the largest relative tilting to be expected of the bite plates the edge of the opening facing towards one of the bite plates engages along its entire circumference with the spherical surface.

Because of the turnable journalling of the balls in the prior-art devices of this type, the exposed spherical surface can extend up from the very tip (located on the longitudinal axis of the pin) of the pin rearwardly only over an angle of 90°. By contrast, the surface of the spherical segment used in the contact pin of the device according to the present invention extends rearwardly beyond the plane of the major circle which extends normal to the pin axis. Only this assures that the tip of the spherical segment will always contact one and the same point on the surface of the other bite plate respectively of a plane assumed to be parallel to and spaced from this surface by a predetermined distance, namely the point corresponding to the traced arrowhead respectively a point at the junction between the aforementioned imaginary plane and a straight line intersecting this plane and the tip of the arrowhead. Moreover, this will be independent of whether the axis of the supporting pin is tilted with reference to the vertical towards the other bite plate or not. Possible deviations in the respective parallel arrangement of the bite plates therefore cannot disadvantageously influence the registration in the vertical (bite height) or in the horizontal (condyle position). Accuracy of registration and fixation on the order of 1/100 millimeter are possible without any difficulties. The error sources of known devices of this type during fixing of the two bite plates after the final bite has been taken, are thus eliminated in a simple and highly effective manner.

Preferably, the spherical surface will extend symmetrically from the forward tip or end of the pin over an angle of 220°–320°, and preferably between 250°–320°. Angles of at least 220° and preferably at least 250° permit even substantial tilting of the bite plates relative to one another during the final bite, without thereby disadvantageously influencing the accuracy of registration and fixation. The aforementioned angles are delimited upwardly only by consideration of strength and simple manufacture. Angles over 320° may cause the material cross-section, over which the spherical segment is in contact with the shaft of the supporting pin, to be too small to be reliable.

It is currently preferred if the spherical segment is seated on its side where it is connected with the shaft of the supporting pin, on a frustonical portion the wider end of which is connected with the shaft of the pin whereas the narrower end of which is connected with the spherical segment and has a smaller diameter than the diameter of the spherical segment itself. This eliminates the danger that during the final bite the edge of the opening might undesirably engage the frustoconical portion. The frustoconical portion or the part of the pin shaft adjacent the spherical segment may be provided with flats which can be engaged by a wrench-like tool to permit adjustment of the supporting pin even when the bite plate is already inserted into the mouth cavity.

The opening which is engageable with the spherical surface of the spherical segment is advantageously formed in known manner in an apertured plate that can be mounted on the other bite plate. According to a variation this opening may, however, also be formed by a bore in the other bite plate itself, the diameter of which is smaller than the diameter of the spherical segment by a predetermined amount. If this construction is chosen, then a suitable tool can be used to produce in the other bite plate at the tip of the arrowhead traced on it during the Gothic arch tracing movement, a hole having a diameter which is smaller than the diameter of the spherical segment by a predetermined figure. During the final bite the spherical segment then enters into this bore to a depth which is fixedly predetermined by the relative relation of spherical segment diameter and bore diameter, and which therefore can be easily taken into account in advance.

To be certain to effect error-free fixing when using an apertured plate, even in the event of more substantial relative tilting of the bite plates, the length of the opening in the apertured plate in the direction of the opening axis should be at most equal to the radius of the spherical segment at the tip of the supporting pin. Also, the length and the diameter of the opening in the apertured plate and the diameter of the spherical segment at the tip of the supporting pin should be so coordinated with one another that when the tip of the supporting pin engages the other bite plate the upper edge of the opening in the apertured plate engages the spherical surface practically without freedom of play. To obtain good retention the thickness of the apertured plate should be equal to the radius of the spherical segment or only slightly smaller than the same.

The apertured plate itself may be constructed as a circular plate which may be self-adhesive, i.e. a member which is provided on one of its major surfaces with a self-adhesive coating preferably covered, until the time of use, by a release paper. The apertured plate may advantageously be of a foil material.

It is particularly advantageous if the bite plates have the form of a planar surface surrounded by the arch of the teeth, the alveolar ridge or the residual rib of an upper respectively lower jaw. This assures a large-area and reliable fixation of the bite plate in the upper and lower jaw during the tracing of the Gothic arch and the final bite, and which is largely immune to tilting moments.

The bite plates, as known from German Gebrausmuster No. 7,709,769, are preferably of a stiff synthetic plastic material. Bite plates of synthetic plastic material are not only substantially less expensive than metallic bite plates, but also greatly facilitate the use of the aligning assembly irrespective of whether in a particular application a toothless jaw is involved, a jaw having some teeth, a jaw having all teeth, a jaw having ground-down teeth or a jaw having a partial or a total prostheses. The bite plates can be trimmed by the dentist very simply in accordance with the particular requirements, for example cutouts can be made to allow them to fit about existing teeth. In this manner the aligning assembly can be universally employed. It is, of course, possible to use different sized bite plates for differently sized jaws, and to keep them in stock. If, however, the bite plates are so dimensioned that they exceed the surface surrounded by the tooth arch of a large upper or lower jaw, by about one centimeter everywhere, then a single aligning assembly size can be used wherein the bite plates are merely trimmed to the desired shape and size when the assembly is to be used.

To obtain the necessary rigidity for synthetic plastic bite plates, which is needed for exact registration, the bite plates may advantageously be reinforced with glass fibers, carbon fibers or metal. In addition, or in lieu thereof, the bite plates may be provided with reinforcing ribs or the like. In particular, it may be advantageous to increase the thickness of the center area of the bite plates. The facing surfaces of the two bite plates are preferably either matte or roughened. This assures a reliable bonding of small quantities of quick-hardening synthetic plastic which may be used to advantage for fixing the bite plates with reference to one another. In addition, it assures good adhesion of the color coating which may be used to help in marking the Gothic arch.

To facilitate the trimming of the bite plates to the desired shape and size, they are either opaque, translucent or transparent in at least their marginal regions.

It has been found to be advantageous if the exterior thread of the supporting pin has a diameter which is slightly (fractions of a millimeter) larger than that of the tapped bore into which the pin is to be threaded. This assures that the pin does not turn too easily and, in turn, prevents the pin from becoming inadvertently repositioned after the Gothic arch has been traced, because this would throw off the results.

For static reasons the tapped bore into which the pin is to be threaded is preferably provided at a part of the one bite plate which is essentially in registry with the center of gravity of the lower jaw. This automatically assures proper centering of the condyles in the sockets.

The tapped bore may be formed in one of the bite plates itself. A more stable mounting of the supporting pin is, however, achieved if the bite plate carrying the supporting pin is provided with a threaded sleeve receiving the supporting pin and which projects from that side of the bite plate facing away from the other bite plate.

If a three-dimensional adjustability of the supporting pin is desired, then it is advantageous to use such a threaded sleeve and mount it in a recess of the one bite plate so that it can be adjusted in two directions of the bite plate plane extending normal to the axis of the supporting pin, and which can be fixed via a clamping portion projecting radially outwardly from the threaded sleeve and a nut that is threaded onto the threaded sleeve itself, with both the clamping portions and the nut having parts extending into the recess of the one bite plate in each desired relative positioning of the threaded sleeve and bite plate, which parts engage for fixing the threaded sleeve with the opposite lateral sides of the one bite plate. Contrary to the construction known from German allowed application No. 2,645,852 this eliminates both the intermediate plate and the clamping members as well as the clamping screws associated with the same. The bite plate itself requires no threaded bore under this arrangement.

The parts overlapping the recess of the one bite plate may be ring flanges or any other projecting portions. A particularly simple use is assured if the threaded sleeve and/or the nut are provided with wing-shaped radial projections which permit a reliable engagement of the threaded sleeve and the nut and thus facilitate their handling. It has been found particularly advantageous to provide the threaded sleeve and/or the nut each with four radial projections spaced about the sleeve or nut at 90 degree angles of offset.

The radial projections of the threaded sleeve may advantageously cooperate in the manner of pointers with two graduations extending at right angles to one another and which are engraved or otherwise formed in the lateral side of the one bite plate facing towards the radial projections. Advantageously the sides of the radial projections facing the graduations have a surface profile which is complementary (e.g. edged) to the graduation. This permits a simple snap-type adjustment of the supporting pin in the bite plate plane. The radial projections together with the graduations serve to prevent undesired turning of the threaded sleeve when the nut is to be turned in order to release the clamping connection between the one bite plate and the unit composed of supporting pin, threaded sleeve and nut, or when the connection is to be tightened.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a perspective view, showing in exploded condition the upper bite plate, the lower bite plate and an apertured plate of a device according to the present invention;

FIG. 2 is an enlarged-scale view, in section, of the assembly of FIG. 1 wherein the tip of the supporting pin engages into the apertured plate;

FIG. 5 is a cross-section through a further embodiment of a bite plate according to the present invention, taken in a section on line V—V of FIG. 6 and having a three-dimensionally adjustable supporting pin;

FIG. 6 is a bottom-plan view of the bite plate of FIG. 5;

FIG. 7 is a top-plan view of the bite plate in FIG. 5; and

FIG. 8 is a fragmentary section of FIG. 5, on an enlarged scale, taken on line VIII—VIII of FIG. 5.

DESCRIPTION OF PREFERRED EMBODIMENTS

Figure 3:
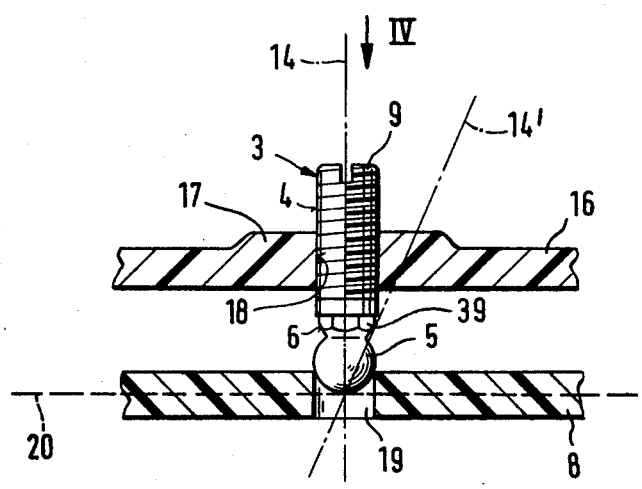
FIG. 3 is a view analogous to FIG. 2 but showing a different embodiment.

Referring firstly to FIGS. 1 and 2 it will be seen that the upper bite plate is identified with reference numeral 1. It is preferably of glass fiber reinforced synthetic plastic material and may have a thickness up to 3 millimeters, or perhaps more. At the side which is facing upwardly in FIG. 2 the plate 1 is provided with a threaded sleeve 7 which is of one piece with it. The threaded sleeve 7 and the adjacent part of the bite plate 1 are provided with a threaded or tapped bore 2 into which a supporting pin 3 is threaded. The pin 3 is provided in the area of its cylindrical shaft 9 with an external thread 4 which permits the user to adjust the spacing of the tip 5 of the supporting pin from the underside of the bite plate 1. The cylindrical shaft 9 merges into a downwardly tapering frustoconical intermediate portion 6 the narrower end of which carries the tip 5 of the pin in form of a spherical segment. The segment 5 has a diameter which is larger than the diameter of the narrow end of the frustoconical portion 6. The exposed spherical surface of the spherical segment 6 extends from the forward tip of the pin, i.e., the tip located on the longitudinal axis 14, on all sides through an angle of at least 100° and preferably at least 125°, so that the rigid connection between the spherical segment 5 and the frustoconical intermediate portion 6 is located on that side of a large circle of the spherical segment 5 normal to the axis 14, which faces away from the tip of the pin. In the region of the portion 6 flaps 39 are provided which permit turning of the pin 3 by means of a not-illustrated tool, e.g. a wrench-like tool.

The lower-jaw bite plate 8 is preferably also made of fiber-reinforced synthetic plastic material and preferably has approximately the same thickness as the bite plate 1. In its upper surface facing the bite plate 1 it may be provided with a coating (not shown) of color serving to facilitate tracing of the Gothic Arch. The bite plates 1 and 8 have a size corresponding to that area surrounded by the dental arch, the alveolar ridge or the residual ridge of an upper jaw, respectively lower jaw, with a dorsal limitation in the tuber and retromolar area. If desired, the bite plates may be produced in indifferent sizes and kept in stock for use with different-sized jaws, except that this is not necessary as explained before. The external thread 4 of the pin 3 has a diameter which is slightly (on the order of fractions of millimeters) larger than the internal diameter of the threads in the tapped bore 2.

The apertured plate may simply be a circular plate or washer 10 provided with a circular center opening 11. The thickness of the plate 10 is smaller than the radius of the spherical segment 5 and the thickness of the plate 10, the diameter of the opening 11 and the diameter of the spherical segment 5 are so coordinated with one another that the upper edge 13 of the opening 11 will engage the spherical surface of the segment 5 without any freedom of play when the tip of the supporting pin rests on the upper side of the bite plate 8. For example, the spherical segment 5 may have a diameter of 1.61 millimeters, in which case the diameter of the opening 11 may be 1.4 millimeters and the thickness of the plate 10 may be 0.4 millimeters. When the lower jaw is closed the segment 5 then enters into the opening 11 to a depth of 0.4 millimeters and, in so doing, engages the upper side of the bite plate 8 at the center of the opening 11. It will be appreciated that other dimensions can also be used and that these given herein are exemplary and not limiting, provided only that it is assured that the exposed spherical surface of the spherical segment 5 projects from the forward tip of the pin 3 (i.e. the tip located on the axis 14) rearwardly to such an extent that even during the largest relative tilting of bite plates 1 and 8 which can be expected, the edge 13 of the opening 11 will still engage the spherical surface of the segment 5 along the entire circumference of the edge 13.

To use the device according to the present invention the bite plates 1 and 8 are mounted in the upper and lower jaws of the patient. If the jaws are without teeth the mounting can be effected by first inserting into the jaw an appropriately shaped base plate of synthetic plastic material which bolts to the jaw by suction. The respective bite plate is then secured to the base plate by means of dental wax or synthetic plastic material. If jaws are to be treated which have some teeth in them the bite plate is cut out to make allowance for the residual teeth, and may be secured by a wax or synthetic plastic wall by means of synthetic plastic material. If the teeth have an advantageous position, then the bite plate can be connected to the teeth directly by means of suitable synthetic plastic material known to those skilled in the dental art. Generally speaking, the bite plate (each of the bite plates) is so mounted as required for the later mounting of the definitive tooth prostheses, i.e. gingival, dental or mixed gingival dental.

When the patient, after the plates have been so mounted, moves his lower jaw as described earlier, then the tip 5 will form on the bite plate 8, respectively in the coating of color provided thereon, the arrow 12 indicated in FIG. 1.

After this is done, a protractor or the like can be used to form a circle of e.g. 2 centimeter diameters about the tip of the arrow, the tip serving as the center of the circle. The plate 10, the diameter of which in this particular example is also advantageously 2 centimeters, is now placed into this circle so as to register with the same and secured to the bite plate 8 with wax or a suitable synthetic plastic. However, the plate 10 could also be of foil material and provided with a self-adhesive coating on one surface. In any case, by securing the plate 10 in this manner the longitudinal central axis of the opening 11 becomes centered on the tip of the arrow 12.

For the final bite the bite plates 1 and 8 are again inserted into the mouth of the patient, and the patient thereupon closes his jaws with slight pressure, causing the tip 5 of the pin to enter into the opening 11 in the manner illustrated in FIG. 2. Two or three drops of synthetic plastic material of the quick-hardening type which have first been placed upon the lower bite plate 8, now connect the bite plates 1 and 8 in the position which has been registered in this manner.

It is essential that the respectively lowermost point of the spherical segment 5 which is rigid with the shaft 9 will always form a tangent to the upper side of the bite plate 8 at the identical point which is predetermined by the opening 11. This point of contact is located on the longitudinal center axis of the opening 11, independently of whether the longitudinal axis 14 of the pin 3 is aligned with the longitudinal axis of the opening 11 as shown in FIG. 2, or assumes an inclined position as for example suggested at 14'. In other words, independently of whether the bite plates 1, 8 are arranged in parallelism with one another or not, and independently of the circular closing movement of the lower jaw, the tip of the pin 3 will always contact the tip of the arrowhead 12 without contacting the apertured plate 10 in a manner capable of flowing off the registration, causing the pin to become inclined and to dislocate the condyles. The space required between the bite plates is only very small.

Figure 4:
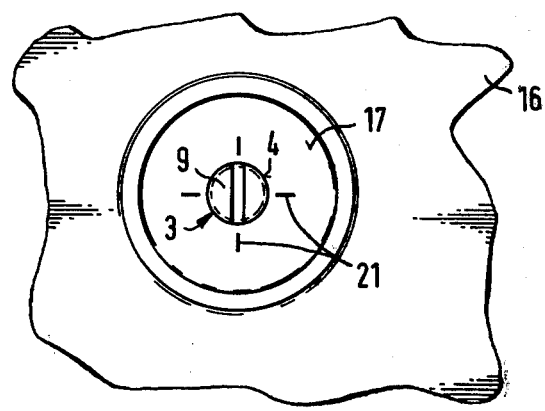
FIG. 4 is a top-plan view of the arrangement of FIG. 3.

In the embodiment according to FIGS. 3 and 4 the apertured plate is omitted. In this embodiment the upper bite plate 16 is provided in the region of the supporting pin 3 with a reinforcement 17 and the pin 3 is mounted by means of a tapped bore 18 in the center of the reinforcement. The marking of the arrowhead is effected in the same manner as described with respect to FIGS. 1 and 2. However, instead of putting an apertured plate in place, concentric to the tip of the arrowhead as described with respect to FIGS. 1 and 2, in FIGS. 3 and 4 a hole is drilled at the registered tip of the arrowhead into the lower bite plate 8. A conventional dental drill used for such purposes can be employed to drill this hole. The diameter of the bore 19, analogously to the diameter of the opening in the apertured plate 10 of FIGS. 1 and 2, is smaller by a predetermined amount than the diameter of the tip 5. During the final bite the spherical segment 5 therefore enters into the bore 19 to an imaginary plane 20 which has a predetermined spacing from that upper side of the bite plate 8 which faces the bite plate 16.

In order to compensate from the depth of penetration of the tip 5 and to assure that the spacing of the bite plates 8 and 16 relative to one another during the tracing of the arrowhead and during the final bite is always the same, the supporting pin 3 is threaded out or forward subsequent to the tracing of the arrowhead and prior to taking the final bite, by a distance which corresponds to the depth of penetration of the tip 5. Preferably, the relation of the diameters of the tip 5 and of the bore hole 19 which determines the depth of penetration of the tip 5 into the bore hole, as well as the turns of the threads of the supporting pin 3, are so coordinated with one another that a trimming of the pin 3 through an angle of e.g. 180° or 360° corresponds to a forward advancement of the pin 3 by an amount equal to the depth of penetration. This readjustment of the pin 3 prior to the patient's taking the final bite is particularly simple if markings are provided at the upper side of the bite plate 16 and possibly also on the supporting pin 3, as indicated with reference numeral 21 in FIG. 4.

A further embodiment of the invention is illustrated in FIGS. 5-8, wherein the upper-jaw bite plate 24 is provided with a quadratic recess 25 through which the supporting pin 3 extends vertically down to the bite plate plane. The pin 3 is threaded into a tapped sleeve 26 and projects with its tip 5 beyond the lower end (FIG. 5) of the tapped sleeve 26. As is shown in the drawing, particularly in FIG. 6, the tapped sleeve 26 is provided with four radial projections 28 which are offset from one another through 90 degree angles and which have sufficient length to extend over the recess 25 in any desired relative position of threaded sleeve 26 and bite plate 24. The end of the tapped sleeve 26 which projects in FIG. 5 beyond the bite plate 24 and is provided with an external thread, has a nut 29 threaded onto it which, in the illustrated embodiment, has radial projections 30 similar to the radial projections 28 of the tapped sleeve 26.

FIGS. 5, 6 and 7 show that in any desired relative position of supporting pin 3 and bite plate 24 the radial projections 28, 30 engage the two broad sides of the bite plate 24. By tightening the nut 29 the position of the axis of the pin 3 can be fixed with respect to the bite plate plane. After releasing the nut 29 the unit composed of pin 3, threaded sleeve 26 and nut 29 can readily be adjusted with reference to the bite plate 24. By threading the pin 3 to a greater or lesser extent out of the tapped sleeve 26, an adjustment of the pin 3 can be effected in a third direction. To facilitate the adjustment of pin 3 and nut 29 these may be provided with transverse flaps 32 and 33, respectively. In order to make it possible to readily adjust the nut 29 even after the bite plate 24 has been inserted into the mouth of the patient, recesses 40 are provided into which complementary projections of a not-illustrated tool can be placed which then serves to turn the nut 29.

The bite plate 24 is provided at the underside cooperating with the radial projections 28 of the threaded sleeve 26, with two graduations 35, 36 which are engraved or otherwise provided and extend at right angles to one another. These each extend to the respective edge of the recess 25. FIG. 8 shows that the radial projections opposite the graduations 35 and 36 have a surface profile 37 which is complementary to the graduation and may, e.g. be blade-like. This means that after the nut 29 is released the pin 3 can be adjusted stepwise in longitudinal and transverse direction of the bite plate 24, with the steps corresponding to the subdivisions of the graduations 35 and 36. It is clear, of course, that the subdivision of the graduations is not limited to the number of steps which are diagrammatically illustrated in FIGS. 6 and 8 for exemplary purposes only. For example, if the recess 25 has an edge length of 15 millimeters, graduations may be provided with fifteen steps in order to permit an adjustment of the pin 3 in the plane of the bite plate 24 by distances each having the length of a millimeter. The graduations 35 and 36, together with the radial projections 28, constitute anti-turning means which prevent a turning of the threaded sleeve 26 during loosening and tightening of the nut 29.

While the invention has been illustrated and described as embodied in an intra-oral aligning assembly, it is not intended to be limited to the details shown, since various modifications and structural changes may be made without departing in any way from the spirit of the present invention.

Without further analysis, the foregoing will so fully reveal the gist of the present invention that others can by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An adjusting assembly for use in prosthodontics, occlusion diagnosis and/or occlusion therapy, comprising an upper jaw plate; a lower jaw plate, one of said plates being provided with an opening; and a pin having an externally threaded shaft partly received in one of the plates and having a free end adapted to be partly received in said opening, said free end being configurated as a spherical segment rigid with said shaft and having a spherical surface, said spherical surface being curved rearwardly from a point located on the longitudinal axis of the shaft through at least 100° of arc, said opening having a diameter being smaller than that of said spherical segment, the diameter and length of said opening as well as the diameter of said segment being so coordinated with one another that even at the largest degree of relative skewing to be expected of said bite plates a circumferential edge of said opening will abut said spherical surface along the entire length of said circumferential edge substantially without any freedom of play.

2. The assembly as defined in claim 1, wherein said spherical surface extends from said point everywhere rearwardly towards said shaft through a range between 220° to 320° of arc.

3. The assembly as defined in claim 1, said shaft having a cylindrical part and an intermediate part between said cylindrical part and said segment, said intermediate part being of frustoconical shape and having a wide end rigid with said cylindrical part and a narrower end rigid with said segment.

4. The assembly of claim 1, wherein said plates are formed of stiffened synthetic plastic material.

5. The assembly of claim 1, wherein said plates are formed of glass fiber reinforced material.

6. The assembly of claim 5, wherein said plates are formed of carbon fiber reinforced material.

7. The assembly of claim 5, wherein said plates are formed of metal reinforced material.

8. The assembly of claim 1, wherein the thickness of said other plate is increased in the center area thereof.

9. The assembly of claim 1, wherein said jaw plates are covered with a coating of color serving.

10. The assembly of claim 1, wherein said jaw plates are opaque in at least their marginal regions.

11. The assembly of claim 1, wherein said jaw plates are translucent in at least their marginal regions.

12. The assembly of claim 1, wherein said jaw plates are transparent in at least their marginal regions.

13. An adjusting assembly for use in prosthodontics, occlusion diagnosis and/or occlusion therapy, comprising an upper jaw plate; a lower jaw plate, a pin having an externally threaded shaft partly received in one of the plates and having a free end adapted to abut the other plate; and a washer adapted to be rigidly connected to said other plate and having an opening formed therein, said free end being configurated as a spherical segment rigid with said shaft and having a spherical surface, said spherical surface being curved rearwardly from a point located on the longitudinal axis of said shaft through at least 100° of arc, so that even at the largest degree of relative skewing to be expected of said bite plates a circumferential edge of said opening will abut said spherical surface along the entire length of said circumferential edge, the thickness of said washer being smaller than the radius of said spherical segment.

14. The assembly as defined in claim 13, wherein the diameter of said opening and the diameter of said segment are so coordinated with one another that said circumferential edge of said opening engages said spherical surface of the spherical segment without any freedom of play when said opening abuts said spherical surface.

15. The assembly of claim 13, wherein said washer has a self-adhesive coating at a surface thereof which is connected to said one plate.

16. The assembly of claim 13, wherein said washer is formed of foil material.

17. An adjusting assembly for use in prosthodontics, occlusion diagnosis and/or occlusion therapy, comprising an upper jaw plate; a lower jaw plate, one of said plates having a recess and the other plate being provided with an opening; a pin having an externally threaded shaft; a tapped and externally threaded sleeve extending through said recess and partly receiving said pin, said pin having a free end adapted to be partly received in said opening; and a nut threaded onto said sleeve, said free end being configurated as a spherical segment rigid with said shaft and having a spherical surface, said spherical surface being curved rearwardly from a point located on the longitudinal axis of said shaft through at least 100° of arc, so that even at the largest degree of relative skewing to be expected of said bite plates a circumferential edge of said opening will abut said spherical surface along the entire length of said circumferential edge, said sleeve being formed with radial clamping projections extending outwardly therefrom, said clamping projections and said nut having parts extending across said recess in each desired relative positioning of said sleeve and said one plate, said parts engaging said one plate for fixing said sleeve with the opposite sides of said one plate.

18. The assembly of claim 1, wherein said upper jaw plate and said lower jaw plate each have a size corresponding to the area surrounded by dental arch, the alveolar process and the residual ridge, respectively.

19. The assembly of claim 17, wherein four said projections are provided which have a wing-shaped radial form.

20. The improvement of claim 19, wherein said projections being offset at 90°.

21. The improvement of claim 17, further comprising two graduations formed in the lateral side of said one plate and extending at right angles to one another and facing towards said radial projections.

22. The improvement of claim 21, wherein said radial projections have a profile on a surface facing said graduations which is complementary to said graduations to simplify a snap-type adjustment of said pin in said other bite.

23. An adjusting assembly for use in prosthodontics, occlusion diagnosis and/or occlusion therapy, comprising an upper jaw plate, and a lower jaw plate; a pin having an externally threaded shaft partly received in one of the plates and having a free end adapted to abut the other plate; and a washer adapted to be rigidly connected to said other plate and having an opening formed therein, said free end being configured as a spherical segment having a spherical surface, said surface being curved rearwardly from a point located on the longitudinal axis of said shaft through at least 100° of arc, so that even at the largest degree of relative skewing to be expected of said plates a circumferential edge of said opening will abut said spherical surface along the entire length of said circumferential edge, said shaft having a cylindrical part and an intermediate part between said cylindrical part and said segment, said intermediate part being of frustoconical shape and having a wide end rigid with said cylindrical part and a narrower end rigid with said segment, said narrower end having a diameter smaller than the diameter of said segment.

24. An adjusting assembly for use in prosthodontics, occlusion diagnosis and/or occlusion therapy, comprising an upper jaw plate, and a lower jaw plate, one of said plates being provided with an opening; and a pin having an externally threaded shaft partly received in the other plate and having a free end adapted to abut said one plate, said free end being configured as a spherical segment rigid with said shaft and having a spherical surface, said spherical surface being curved rearwardly from a point located on the longitudinal axis of the shaft through at least 100° of arc, so that even at the largest degree of relative skewing to be expected of said bite plates a circumferential edge of said opening will abut said spherical surface along the entire length of said circumferential edge, said shaft having a cylindrical part and an intermediate part between said cylindrical part and said segment, said intermediate part being of frustoconical shape and having a wide end rigid with said cylindrical part and a narrower end rigid with said segment, said narrower end having a diameter smaller than the diameter of said segment.

25. An adjusting assembly for use in prosthodontics, occlusion diagnosis and/or occlusion therapy, comprising an upper jaw plate, and a lower jaw plate, one of said plates being provided with an opening; a pin having an externally threaded shaft; and a sleeve connected to the other plate and having a free end adapted to abut said one plate, said shaft being partly received in said sleeve, said free end being configured as a spherical segment rigid with said shaft and having a spherical surface, said surface being curved rearwardly from a point located on the longitudinal axis of the shaft through at least 100° of arc, so that even at the largest degree of relative skewing to be expected of said bite plates a circumferential edge of said opening will abut said spherical surface along the entire length of said circumferential edge, said shaft having a cylindrical part and an intermediate part between said cylindrical part and said segment, said intermediate part being of frustoconical shape and having a wide end rigid with said cylindrical part and a narrower end rigid with said segment, said narrower end having a diameter smaller than the diameter of said segment, said sleeve having four outwardly radially extending projections, said projections being offset from one another through 90°.

26. An adjusting assembly for use in prosthodontics, occlusion diagnosis and/or occlusion therapy, comprising an upper jaw plate; a lower jaw plate; a pin having an externally threaded shaft partly received in one of the plates and having a free end adapted to abut the facing surface of the other plate; and a washer adapted to be rigidly connected to said surface of the other plate, said free end being configured as a spherical segment rigid with said shaft and having a spherical surface, said spherical surface being curved rearwardly from a point located on the longitudinal axis of the shaft through at least 100° of arc, so that even at the largest degree of relative skewing to be expected of said bite plates a circumferential edge of said opening will abut said spherical surface along the entire length of said circumferential edge, the thickness of said washer being smaller than the radius of said spherical segment, the diameter of said opening and the diameter of said segment being so coordinated with one another that said circumferential edge of said opening engages said spherical surface of the spherical segment without any reedom of play when said segment abuts said surface of the other plate.

27. The assembly as defined in claim 1, wherein said one plate has a tapped bore, and the external thread of said shaft has a diameter which is slightly larger than that of said bore which receives said shaft.

28. The assembly as defined in claim 27, wherein said tapped bore is formed at a part of said one plate which is essentially in registry with the center of gravity of the lower jaw to thereby automatically provide proper centering of the condyles in the sockets.

29. The assembly as defined in claim 1, wherein said one plate is formed with a sleeve which receives said pin, said sleeve projecting from that side of said one plate which faces away from said other plate.

30. A method of defining a proper position of a lower jaw plate in an adjusting assembly for use in prosthodontics, occlusion diagnosis and/or occlusion therapy including said lower jaw plate and an upper jaw plate, a pin partly received in one of said plates and having an externally threaded shaft having a free end being configured as a spherical segment having a spherical surface being curved rearwardly from a point located on the longitudinal axis of the shaft through at least 100° of arc, the method comprising the steps of cutting out said plates to make allowance for the residual teeth in a mouth of a patient; mounting said upper jaw plate and said lower jaw plate in the patient's mouth; moving said free end so that it abuts said other plate and defining a predetermined place on said other plate; removing said other plate from the patient's mouth; drilling an opening at said predetermined place of said other plate, and perpendicular to the surface of said other plate the diameter and length of said opening and the diameter of said segment being so coordinated with one another that even at the largest degree of relative skewing to be expected of said plates a circumferential edge of said opening will abut said circumferential edge substantially without any freedom of play when said opening abuts said spherical surface; mounting said other plate into the mouth of the patient; and moving said other plate thereby causing said segment to enter into said opening; connecting said plates in a registered position; and removing said plates from the mouth of the patient.

31. The method of claim 30, wherein before said segment enters said opening said shaft is threadably moved from said one plate at a distance substantially equal to the path of entering of said segment into said opening.

32. A method of defining a proper position of a lower jaw plate in an adjusting assembly for use in prosthodontics, occlusion diagnosis and/or occlusion therapy including an upper jaw plate and the lower jaw plate; a pin having an externally threaded shaft partly received in one of the plates and having a free end adapted to abut the other plate, and a washer adapted to be rigidly connected to said other plate and having an opening formed therein, said free end being configured as a spherical segment having a spherical surface being curved rearwardly from a point located on the longitudinal axis of the shaft through at least 100° of arc, the thickness of said washer being smaller than the radius of said spherical segment, the diameter of said opening and the diameter of said segment being so coordinated with one another that the circumferential edge of said opening engages said spherical surface of said segment without any freedom when said segment abuts said othter plate, the method comprising the steps of cutting out said plates to make allowance for the residual teeth in a mouth of a patient; mounting said upper jaw plate and said lower jaw plate in the patient's mouth; moving said free end of said shaft so that it abuts said other plate and defining a predetermined place on said other plate; removing said other plate from the patient's mouth; placing said washer on said predetermined place so as to register said opening with said plate and securing said washer to said other plate; mounting said other plate into the mouth of the patient and moving said other plate thereby causing said segment to enter into said opening; connecting said plates in a registered position; and removing said plates from the mouth of the patient.

33. An adjusting assembly for use in prosthodontics, occlusion diagnosis and/or occlusion therapy, comprising an upper jaw plate and a lower jaw plate, one of said plates being provided with an opening, and a pin having an externally threaded shaft partly received in the other plate and having a free end adapted to abut said one plate, said free end being configured as a spherical segment rigid with said shaft and having a spherical surface, said spherical surface being curved rearwardly from a point located on the longitudinal axis of the shaft through at least 100° of arc, so that even at the largest degree of relative skewing to be expected of said bite plates a circumferential edge of said opening will abut said spherical surface along the entire length of said circumferential edge, the diameter of said opening and the diameter of said segment being so coordinated with one another that said circumferential edge of said opening engages said spherical surface of the spherical segment without any freedom of play when said openings abut said spherical surface.

* * * * *